US00PP29651P2

(12) United States Plant Patent
Cain

(10) Patent No.: US PP29,651 P2
(45) Date of Patent: Sep. 11, 2018

(54) GRAPEVINE 'IFG TWENTY-NINE'

(50) Latin Name: ***Vitis interspecific* hybrid**
Varietal Denomination: IFG Twenty-nine

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/732,051

(22) Filed: Sep. 11, 2017

(51) Int. Cl.
*A01H 5/08* (2018.01)

(52) U.S. Cl.
USPC ..... Plt./207

(58) Field of Classification Search
USPC ..... Plt./207
See application file for complete search history.

*Primary Examiner* — Annette H Para

(57) ABSTRACT

This invention is a new and distinct grapevine variety denominated 'IFG Twenty-nine'. The new grapevine is characterized by producing extremely narrow elongated, medium firm, white, seedless fruit with a characteristic pointed tip and pleasant mild flavor.

1 Drawing Sheet

Latin name of the genus and species claimed: *Vitis interspecific* hybrid.

Variety denomination: 'IFG Twenty-nine'.

BACKGROUND OF THE INVENTION

The new and distinct grapevine described and claimed herein originated from a hand pollinated cross of the Calinda variety and Arkansas 2409, an unnamed interspecific hybrid seedless grape selection, hybridized in May 2002. The abortive seed traces were subsequently embryo cultured and the resulting sixty-nine plants were planted in the field in April 2003. The present variety of grapevine was selected as a single plant in July 2004 and was first asexually propagated by hardwood cuttings in December 2004. The resulting propagules were planted during April 2005 near Delano, Kern County, Calif. and were found to reproduce true-to-type through at least two generations of asexual reproduction.

BRIEF SUMMARY OF THE INVENTION

The new grapevine 'IFG Twenty-nine' is characterized by producing extremely narrow elongated seedless fruit with a characteristic pointed tip. The unusual shape provides consumers with a distinct visual signal to identify the new variety. The new variety is further characterized by producing medium firm white fruits which ripen in midseason season. Berries are moderately crisp in texture, mild flavored and may have small to medium size rudimentary seed traces. Bunches are long and are naturally loose so require no gibberellin for berry thinning. Vines of 'IFG Twenty-nine' are productive. The fruit are naturally large and does not require treatment with gibberellic acid to obtain satisfactory size. The new grapevine variety is being introduced to provide home gardeners with a high quality seedless grape with a distinctive shape.

'IFG Twenty-nine' differs from its maternal parent by producing very elongated narrow pointed white berries having small to medium seed traces as opposed to the red elongated fruits having very large seed traces of the Calinda variety. It differs from its pollen parent by possessing firmer berries with white coloration as opposed to the narrow, elongate pointed black fruits of A2409. The skin of 'IFG Twenty-nine' is thinner and the taste is less herbaceous than the A2409.

BRIEF DESCRIPTION OF THE DRAWING

The accompanying photographic drawing in FIG. 1 illustrates in full color 'IFG Twenty-nine'. The photograph was taken outdoors with indirect lighting. The colors are as nearly true as is reasonably possible in a color representation of this type. The left side of the drawing has mature leaves. A mature fruit cluster is represented in the center of the drawing along with a typical berry in cross section. A young shoot can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification, subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty-nine' plants grown in the vicinity of Delano, Kern County, Calif. during 2012, and is believed to apply to plants of the variety grown under similar conditions of soil and climate elsewhere:

VINE

General:

*Vigor*.—Vigorous.

*Density of foliage*.—Medium.

*Productivity*.—Productive, producing about 24.3 to 36.5 kg of fruit per vine.

*Rootstock*.—Own root.

*Training method*.—Typically spur pruned leaving 2 bud spurs.

Trunk:

*Trunk diameter of* 4-*year-old vines at* 30 *cm above the soil line*.—About 3.8 cm.

*Shape*.—Stocky.

*Straps*.—Very long.

*Surface texture*.—Shaggy.

*Inner bark color*.—The following colors were observed: Greyed-orange: 166B and 166C.

SHOOTS

Young shoot:

*Form of tip*.—Fully opened.

*Distribution of anthocyanin coloration of tip*.—Overall.

*Intensity of anthocyanin coloration of tip*.—Medium to strong.

*Density of prostrate hairs of tip*.—Dense.

*Density of erect hairs of tip*.—Absent.

*Color*.—The following colors were observed: Green: 144A and 146A.

Woody shoot (mature canes):

*Shape*.—Stocky.

*Internode length*.—Long: About 10.3 cm.

*Width at node*.—About 0.7 cm.

*Cross section*.—Elliptic.

*Surface*.—Striate.

*Main color*.—The following colors were observed: Greyed orange: 166C and 164A and 164B.

*Density of erect hairs on nodes*.—None or very sparse.

*Density of erect hairs on internodes*.—None or very sparse.

*Growth of axillary shoots*.—Weak to medium: Approximately 11.9 cm.

Flowering shoot:

*Vigor during flowering*.—Medium.

*Attitude during flowering on shoots not tied*.—Erect to semi-erect.

*Color*.—Dorsal side of internodes: Yellow-green: 146C, with Greyed-purple stripes: 183A.

*Color*.—Ventral side of internodes: Yellow-green: 146C.

*Color*.—Dorsal side of nodes: Yellow-green: 146C, with Greyed-purple stripes: 183A.

*Color*.—Ventral side of nodes: Yellow-green: 146C.

*Density of prostrate hairs on nodes*.—Sparse.

*Density of erect hairs on nodes*.—Sparse.

*Density of prostrate hairs on internode*.—Very sparse.

*Density of erect hairs on internode*.—None.

*Anthocyanin coloration of buds*.—Absent.

Tendrils (at full bloom):

*Distribution on the shoot* (*at full flowering*).—Discontinuous.

*Length of tendril*.—Long: About 27.7 cm.

*Thickness of tendril* 2 *cm from base*.—About 2.6 mm.

*Color*.—The following colors were observed: Yellow-green: 144A and 144B, and Greyed-purple 183A.

*Form*.—Trifurcated.

*Number of consecutive tendrils*.—2.

LEAVES

Young leaves:

*Color of upper surface of first four distal unfolded leaves*.—Yellow-green: 146A and Greyed-purple: 183A.

*Average intensity of anthocyanin coloration of six distal leaves prior to flowering*.—Medium.

*Density of prostrate hairs between veins* (*lower surface*).—Dense.

*Density of prostrate hairs on veins* (*lower surface*).—Dense.

*Density of erect hairs between veins* (*lower surface*).—Absent.

*Density of erect hairs on veins* (*lower surface*).—Absent.

Mature leaves (opposite first cluster):

*Average length*.—About 15.5 cm.

*Average width*.—About 18.9 cm

*Mature leaf size*.—Medium.

*Shape of blade*.—Pentagonal.

*Number of lobes*.—5.

*Blade venation*.—Palmate.

*Anthocyanin coloration of main veins on upper side of blade*.—Slight to medium.

*Mature leaf profile*.—Flat to undulate.

*Blistering surface of blade upper surface*.—Weak to medium.

*Leaf blade tip*.—Curved downwardly.

*Undulation of margin*.—Slight.

*Undulation of blade between main and lateral veins*.—Overall.

*Shape of teeth*.—Mixture of both sides straight and both sides convex.

*Length of teeth*.—Long.

*Ratio length/width of teeth*.—Large.

*Shape of upper lateral sinuses*.—Open.

*Depth of upper lateral sinuses*.—Deep.

*General shape petiole sinus*.—Slightly overlapped.

*Shape of base of upper leaf sinuses*.—V-shaped.

*Tooth at petiole sinus*.—Absent.

*Density of prostrate hairs between veins on lower surface of blade*.—Sparse to medium.

*Density of erect hairs between veins on lower surface of blade*.—Absent.

*Density of prostrate hairs on main veins on lower surface of blade*.—Medium.

*Density of erect hairs on main veins on lower surface of blade*.—Very sparse.

*Density of prostrate hairs on main veins on upper surface of blade*.—None or very sparse.

*Density of erect hairs on main veins on upper surface of blade*.—None.

*Autumn coloration of leaves*.—Leaves can be a single color or combination of colors, in a mottled pattern or on the edges of the leaves: The following colors were observed: Yellow: 10A and 10B, and 14A and 14B and Greyed-orange: 166A.

Upper surface:

*Color*.—The following colors were observed: Green: 139A and Yellow-green: 147A.

*Anthocyanin coloration of main veins*.—Very weak.

*Color of main veins*.—Yellow-green: 144C.

*Surface appearance*.—Semi-glossy to dull.

*Blistering surface of blade*.—Weak to medium.

Lower surface:

*Color*.—The following colors were observed: Green 138A and 137C.

*Anthocyanin coloration of main veins* (*lower surface*) .—Weak.

*Color of main veins*.—Yellow-green: 145C.

*Glossiness*.—Weak.

*Surface texture*.—Rugose.

*Surface appearance*.—Dull.

Petiole:

*Length*.—About 11.8 cm.

*Diameter of petiole* 2 *cm from blade*.—About 5.0 mm.

*Petiole color*.—The following colors were observed: Yellow-green: 148C and Red-purple: 59B.

*Length of petiole compared to middle vein*.—Moderately shorter.

*Density of prostrate hairs on petiole*.—None.

*Density of erect hairs on petiole*.—None.

Buds:

*Bud fruitfulness*.—Basal: Mostly fruitful.

*Position of first fruitful shoot on previous season cane*.—$1^{st}$ to $2^{nd}$ node.

*Dormant bud length*.—About 3.8 mm.

*Dormant bud width in the proximal/distal plane*.—About 3.8 mm.

*Dormant bud color*.—Greyed-orange: 166A.

*Time of bud burst*.—Early: Mar. 12, 2012.

FLOWERS

General:

*Flower sex*.—Hermaphrodite.

*Length of first inflorescence*.—Medium: About 18.7 cm long by 9.3 cm wide.

*Position of first flowering and fruiting node*.—$3^{rd}$ to $4^{th}$ node (current season growth).

*Number of inflorescence per flowering shoot*.—1.1 to 2.

*Time of bloom*.—Late as compared with similar varieties in the growing area of Delano, Calif.

*Date of full bloom*.—May 18, 2012.

FRUIT

General:

*Ripening period*.—Mid-season: Approximately Aug. 14, 2012.

*Use*.—Home gardening.

*Keeping quality*.—Good.

*Resistance to*.—Insects: Average typical of *Vitis vinifera* species. Diseases: Average typical of *Vitis vinifera* species.

*Refractometer test*.—Solid-sugar: About 16.2 Brix.

*Brix/acid*.—About 33.7.

*Titratable acidity*.—About 0.48.

*Juice ph*.—About 3.6.

Cluster:

*Mature cluster length* (*peduncle excluded*).—About 29.4 cm.

*Mature cluster width*.—About 16.2 cm.

*Mature cluster weight*.—About 810 g.

*Bunch density*.—Medium.

*Number of berries*.—About 130.

*Form*.—Conical.

Peduncle:

*Lignification of peduncle*.—Weak.

*Length of peduncle*.—Medium: Approximately 3.1 cm.

Berry:

*Uniformity of size*.—Uniform.

*Single berry weight*.—About 6.8 g natural: to about 11.4 g when treated with gibberellic acid.

*Shape*.—Range of cylindrical and finger-shaped berries, few have horn-shaped appearance.

*Seeds*.—Contains small rudimentary seed traces, seed traces occasionally noticeable.

*Cross section*.—Circular.

*Berry dimensions*.—Longitudinal axis: About 4.4 cm. horizontal axis: About 1.6 cm.

*Berry firmness*.—Medium.

*Particular flavor*.—Neutral.

*Bloom* (*cuticular wax*).—Absent to very weak.

*Berry separation from pedicel*.—Somewhat easy.

*Skin color* (*without bloom*).—The following colors were observed: Yellow-green: 145B and 145C.

Skin:

*Thickness*.—Medium.

*Texture*.—Medium.

*Reticulation*.—Absent.

*Tenacity*.—Tenacious to flesh.

What is claimed:

1. A new and distinct variety of grapevine as herein illustrated and described.

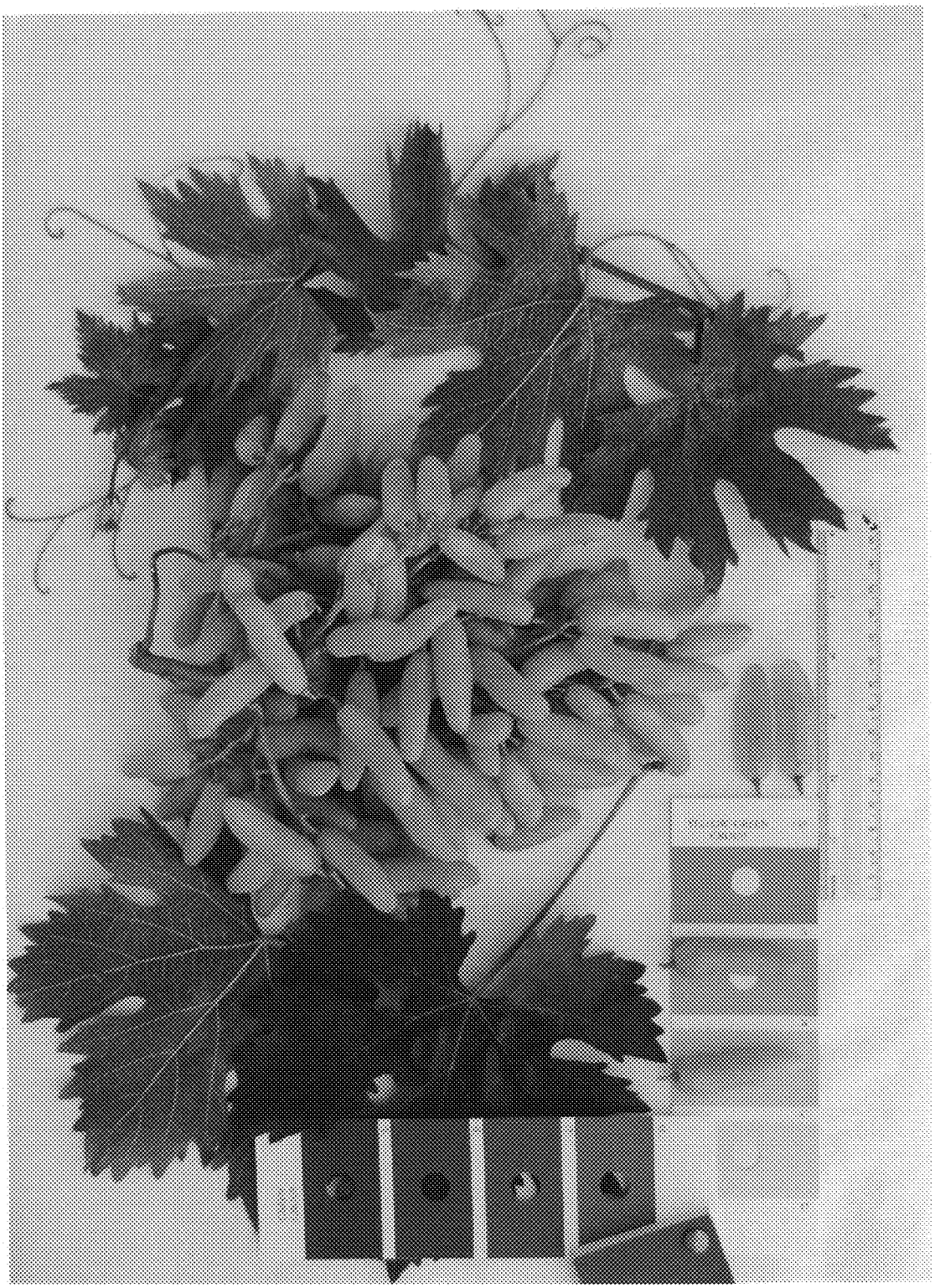

* * * * *